US 6,737,046 B2

(12) United States Patent
Schmenger et al.

(10) Patent No.: US 6,737,046 B2
(45) Date of Patent: May 18, 2004

(54) COMPOSITION FOR A HAIR TREATMENT PREPARATION IN THE FORM OF AN AEROSOL FOAM

(75) Inventors: Juergen Schmenger, Weiterstadt (DE); Wilhelm Abels, Simi Valley, CA (US); Mehrdad Jahedshoar, Calabasas, CA (US)

(73) Assignee: Wella Aktiengellschaft, Darmstadt (DE)

( * ) Notice: Subject to any disclaimer, the term of this patent is extended or adjusted under 35 U.S.C. 154(b) by 0 days.

(21) Appl. No.: 09/937,228

(22) PCT Filed: Jan. 4, 2001

(86) PCT No.: PCT/EP01/00032

§ 371 (c)(1),
(2), (4) Date: Jan. 28, 2002

(87) PCT Pub. No.: WO01/52800

PCT Pub. Date: Jul. 26, 2001

(65) Prior Publication Data

US 2002/0197213 A1 Dec. 26, 2002

(30) Foreign Application Priority Data

Jan. 21, 2000 (DE) ........................................ 100 025 137

(51) Int. Cl.$^7$ .............................. A61K 7/00; A61K 9/00; A61K 7/06; A61K 7/11; A61K 7/075
(52) U.S. Cl. ..................... 424/47; 424/70.1; 424/70.11; 424/70.12; 424/70.27; 424/400; 424/401; 424/DIG. 1; 424/DIG. 2
(58) Field of Search .................. 424/400, 401, 424/70.1, 70.11, 70.12, 70.27, 47, DIG. 1, DIG. 2

(56) References Cited

U.S. PATENT DOCUMENTS

| 5,254,333 | A | * | 10/1993 | Kajino et al. | ............ | 424/70.11 |
| 5,876,463 | A | * | 3/1999 | Garcia et al. | ................... | 8/405 |
| 6,436,151 | B2 | * | 8/2002 | Cottard et al. | ................. | 8/406 |
| 6,528,046 | B1 | * | 3/2003 | Schmenger et al. | ....... | 424/70.1 |

FOREIGN PATENT DOCUMENTS

| EP | 0 680 743 A | 11/1995 |
| EP | 0 745 373 A | 12/1996 |
| EP | 0 978522 A1 | 2/2000 |
| WO | 96/40815 | 12/1996 |
| WO | 96 40815 A | 12/1996 |
| WO | 99/40892 | 8/1999 |

OTHER PUBLICATIONS

Schrader "Grundlagen Und Rezepturen Der Kosmetika", 2. Auglage, 1989, pp. 728–737.
E. Flick: "Cosmetic and Toiletry Formulations", Second Edition, vol. 2, pp. 373–378; 1992.

* cited by examiner

*Primary Examiner*—Thurman K. Page
*Assistant Examiner*—Marina Lamm
(74) *Attorney, Agent, or Firm*—Michael J. Striker

(57) ABSTRACT

Described is a composition for a hair-treatment preparation which is preferably in the form of an optically clear, transparent or translucent product that can be used as an aerosol foam and contains (A) at least one nonionic, amphiphilic associative thickener in an appropriate cosmetic carrier and (B) at least one propellant. The preparation can be used as a leave-in hair treatment or as a hair rinse which condition the hair and confers to it luster and volume.

12 Claims, No Drawings

COMPOSITION FOR A HAIR TREATMENT PREPARATION IN THE FORM OF AN AEROSOL FOAM

BACKGROUND OF THE INVENTION

The object of the invention is a composition for a hair treatment preparation which preferably is in the form of an optically clear, transparent or translucent product and is used as an aerosol foam. In particular, the preparation can be a hair-care preparation usable as a leave-in hair treatment or as a hair rinse. The composition contains certain associative thickeners and propellants and optionally cationic hair-care agents and hydrophilic silicones.

As a rule, common hair-conditioning preparations, such as rinse-off treatments or leave-on treatments, are formulated on the basis of aqueous emulsions. Essential ingredients are cationic substances, for example cationic surfactants, hydrophobic substances, for example fatty alcohols, and other oil components, emulsifiers and other specific active ingredients and perfumes. The most important ingredients are the cationic surfactants, fatty alcohols and emulsifiers. A review of the general make-up of rinsing treatments and hair treatments can be found in Schrader, "Grundlagen und Rezepturen der Kosmetika" [Fundamentals and Formulations of Cosmetics], 2nd edition, 1989, pages 728 to 737. The main function of conditioners is to improve the stylability, combability, luster and feel of the treated hair. The treated hair often feels somewhat heavier and more burdened which is not always desirable. Moreover, the conventional oil-in-water [O/W] hair care emulsions are normally milky-white and opaque. Desirable are products which are in an visually attractive form and clear, transparent or at least translucent. Various forms of clear hair care preparations are known and are described, for example, in E. Flick, "Cosmetic and Toiletry Formulations", second edition, volume 2, pages 373 ff. The preparation of these clear hair care formulations is based on the use of thickening-type polymers, such as, for example, cellulose derivatives (tradenames Natrosol®, Methocel®), high-molecular-weight chitosan derivatives (tradename Kytamer® PC), complex polysaccharides (commercial names karaya gum, tragacanth, Jaguar® brands, Keltrol® brands) and acrylic acid polymers. The major drawback of all these described clear hair care preparations is that their care effect is so weak that it does not come anywhere near the effect of conventional hair care preparations based on mixtures of fatty alcohols and quaternary surfactants. For this reason, in the marketplace these prior-art clear hair care preparations definitely do not sell as well as the standard treatments.

SUMMARY OF THE INVENTION

It has been found that it is possible, by use of nonionic, amphiphilic associative thickeners, to produce preparations which meet the typical requirements placed on hair conditioners in terms of hair conditioning and which, at the same time, can be in a visually attractive form and confer to the hair a less heavy, less burdened feel than that resulting from treatment with a conventional hair care preparation. It has been found, however, that such preparations are not yet entirely satisfactory in terms of emulsification while they are being worked into the hair. The product does not feel sufficiently substantial, namely the amount of emulsion is too small.

We have now found that these drawbacks can be eliminated by use of a hair treatment composition based on a combination of associative thickeners and propellants commonly used with aerosol foams. The object of the invention is therefore a composition for a hair treatment preparation containing (A) at least one nonionic, amphiphilic associative thickener in an appropriate cosmetic carrier and (B) at least one propellant.

The composition of the invention preferably contains additionally at least one hair-care substance (C) containing at least one cationic group and/or at least one hair-care silicone compound (D) with at least one hydrophilic group. The combination of the invention was found to have outstanding foaming properties even without an added surfactant, making the combination particularly well suited for preparing aerosol foam products.

The associative thickener (A) is preferably contained in the composition of the invention in an amount from 0.1 to 5 wt. % and particularly from 0.1 to 2 wt. %. The propellant is preferably present in an amount from 0.05 to 40 wt. % and particularly from 0.2 to 10 wt. %. The cationic substance (C) is preferably contained in the composition of the invention in an amount from 0.01 to 10 wt. % and particularly from 0.1 to 5 wt. %, and the silicone compound (D) preferably in an amount from 0.01 to 10 wt. % and particularly from 0.1 to 5 wt. %.

A hair treatment preparation made with the composition of the invention meets the requirements placed on hair conditioners in terms of the conditioning effect in the best manner and shows improved emulsification during use. After the treatment, the hair, in both the moist and the dry state, is noticeably smoother, and the wet combability is noticeably improved. Surprisingly, we have now found that the thickener makes it possible to incorporate the cationic substances and the said silicone compound without bringing about the negative side effects of the thickener. The technical properties of the preparation of the invention even exceed those of a conventional hair treatment based on an aqueous emulsion of fatty alcohols and quaternary surfactants. Comparative beauty salon tests performed side by side on the same scalp confirmed the better combability and more natural feel of hair treated with the preparation of the invention. The negative, dull feel of hair treated with fatty alcohol/cationic surfactant mixtures is practically eliminated when the preparation of the invention is used. The hair feels lighter and less burdened. Moreover, the combination of the invention in the form of an aerosol foam makes it possible to package the preparation in the form of a visually attractive, clear formulation which in turn permits advantageous packaging in a transparent container, for example one of glass or transparent plastic, for example polyethylene, polypropylene or polyethylene terephthalate. The aerosol foam application form is particularly advantageous for hair treatment. While being worked into the hair, the preparation packaged without the propellant feels less substantive and does not contain sufficient emulsion. Tests run by trained hair dressers have shown that the aerosol foam application form is clearly preferred.

The nonionic, amphiphilic associative thickener (A) is a polymer containing both hydrophilic and hydrophobic groups. Associative thickeners are water-soluble polymers containing surfactant-like hydrophobic constituents which in a hydrophilic and particularly in an aqueous medium are capable of associating, namely interacting, with themselves as wall as with other hydrophobic substances. The resulting associative network causes the medium to thicken or gel. Typically, associative thickeners are prepared by polymerization of polyethylene oxide propolymers and at least difunctional, polycondensable substances, for example isocyanates, whereby monohydric alcohols or diols with large aryl, alkyl or aryl/alkyl groups are incorporated so as to produce the hydrophobic modification. Hence, hydrophobically modified polyalkylene glycols are the preferred associative thickeners. The hydrophilic moiety is thus formed of polyoxyalkylene units, preferably of polyoxyethylene but also polyoxypropylene units or of a mixture thereof. The hydrophobic moiety is preferably formed of hydrocarbon groups, for example long-chain alkyl groups, alkylaryl or arylalkyl groups.

Particularly preferred associative thickeners are hydrophobically modified aminoplast—polyether copolymers. Regarding their structure and preparation, the reader is referred to WO 96/40815. In WO 96/40815 are described water-dispersible or water-soluble copolymers formed as products of an acid-catalyzed polycondensation of an at least difunctional aminoplast monomer, an at least difunctional alkylene polyether and a monofunctional compound with hydrophobic groups. Suitable aminoplasts are shown in FIG. 1 of WO 96/40815. Particularly preferred are the glycoluril derivatives of formula X in WO 96/40815. Suitable alkylene polyethers are the polyethylene oxide diols. These can have a degree of ethoxylation from 20 to 500, preferably from 60 to 350 and particularly from 100 to 250. Suitable monofunctional compounds with hydrophobic groups are those of formula XIV in WO 96/40815.

According to the invention, suitable associative thickeners are selected from among polymers of general formula (I)

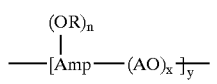

(I)

wherein Amp denotes an aminoplast monomer or the radical of an aminoplast oligomer or polymer, AO denotes an alkylene oxida group, R denotes hydrogen, $C_1$–$C_4$-alkyl or $C_1$–$C_4$-acyl and x and y denote numerals greater than 1.

Particularly preferred are the reaction products formed by acid-catalyzed polycondensation of (a) a glycoluril of general formula (II)

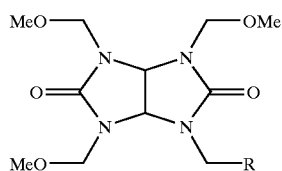

(II)

wherein R stands for H or preferably for OMe, (b) a polyethylene oxide diol with a degree of ethoxylation from 20 to 500, preferably from 50 to 350 and particularly from 100 to 250, and (c) an optionally ethoxylated hydrophobic alcohol, alkylphenol, thiol, carboxamide, carbamate or hydrophobic carboxylic acid such as those described on pages 17 to 19 of WO 96140815. The particularly preferred glycoluril is 1,3,4,6-tetramethoxymethylglycoluril.

Suitable associative thickeners are those with an INCI name of polyether 1, PEG 180/octoxynol-40/TMMG copolymer and PEG 180/laureth 50/TMMG copolymer sold by Süd-Chemie under the tradenames Pure-Thix® HH, L and M.

Usable propellants (B) are, for example, the lower alkanes, for example n-butane, i-butane and propane or a mixture thereof, as well as dimethyl ether or a fluorohydrocarbon such as F 152a (1,1-difluoroethane) or F 134 (tetrafluoroethane), furthermore propellants which at the pressures involved are gaseous, for example $N_2$, $N_2O$ and $CO_2$, as well as mixtures of the aforesaid propellants. n-Butane, i-butane and propane, particularly propane/butane mixtures, and dimethyl ether, and mixtures thereof are preferred.

The cationic material (C) is a substance which because it contains cationic or cationizable groups, particularly primary, secondary, tertiary or quaternary amino groups, exhibits substantivity for human hair. Suitable cationic materials are selected from among cationic surfactants, betaine surfactants, amphoteric surfactants, cationic polymers with cationic or cationizable groups, cationically derivatized proteins, cationically derivatized protein hydrolyzates and betaine.

Suitable cationic surfactants are those containing a quaternary ammonium group. They include cationic or amphoteric betaine surfactants. Particularly preferred cationic materials (C) are cationic surfactants. Suitable cationic surfactants contain amino groups or quaternized hydrophilic ammonium groups which in solution bear a positive charge and are represented by general formula (III)

(III)

wherein $R^1$ to $R^4$ independently of each other denote aliphatic groups, aromatic groups, alkoxy groups, polyoxyalkylene groups, alkylamido groups, hydroxyalkyl groups, aryl groups or alkaryl groups with 1 to 22 carbon atoms, and $X^{(-)}$ denotes an anion, for example a halogen, acetate, phosphate, nitrate or alkylsulfate, and preferably chloride. Besides the carbon atoms and hydrogen atoms, the aliphatic groups can contain linking groups or other groups, for example hydroxyl groups, or other amino groups.

Examples of suitable cationic surfactants are alkyldimethylbenzylammonium chlorides or bromides, the alkyltrimethylammonium salts, for example cetyltrimethylammonium chloride or bromide, tetradecyltrimethylammonium chloride or bromide, alkyldimethylhydroxyethylammonium chlorides or bromides, the dialkyldimethylammonium chlorides or bromides, the alkylpyridinium salts, for example lauryl-pyridinium or cetylpyridinium chloride, the alkylamiddothyltrimethylammonium ether sulfates as well as compounds with a cationic character, such as amine oxides, for example alkylmethylamine oxides or alkylaminoethyldiethylamine oxides. Particularly preferred is cetyltrimethylammonium chloride which, for example in the form of a 26% aqueous solution, is sold by Henkel KGaA, Düsseldorf, Germany, under the tradename Dehyquart® A and by Hoechst A G, Frankfurt, Germany, under the tradename Genamin® CTAC, and in the form of a 50% solution in isopropanol by Akzo Chemicals GmbH, Düren, Germany, under the tradename Arquad® 16-50.

Other suitable cationic surfactants are those known as esterquats. By esterquats are meant, in general, quaternized fatty acid triethanolamine ester salts. Esterquats are known, for example, from WO 91/01295. Suitable esterquats are those of general formula (VIII)

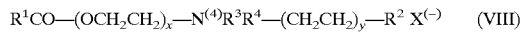

(VIII)

wherein $R^1CO$ denotes an, optionally hydroxy-substituted, $C_6$–$C_{22}$-acyl group, $R^2$ denotes hydrogen or an $R^1CO$ group, $R^3$ denotes a $C_1$–$C_4$-alkyl group or the $(CH_2CH_2O)_z$—H group, $R^4$ denotes a $C_1$–$C_4$-alkyl-group or the $(CH_2CH_2O)_q$—$R^2$ group, X[+] is a suitable anion, for example halogen, alkylsulfate or alkylphosphate, and x, y, z and q stand for a numeral from 1 to 12. Particularly preferred are ester-quats wherein $R^1CO$ denotes a $C_{12}$–$C_{20}$-acyl group, $R^2$ denotes an $R^1CO$ group, $R^3$ denotes $CH_2CH_2OH$, $R^4$ denotes methyl, $X^{(-)}$ denotes methylsulfate and x and y stand for the numeral 1. Such compounds are available commercially under the tradenames Dehyquart® L, Dehyquart® F, Schercoquat® and Tetranyl®.

Suitable amphoteric surfactants are the derivatives of aliphatic quaternary ammonium, phosphonium and sulfonium compounds of formula (IV)

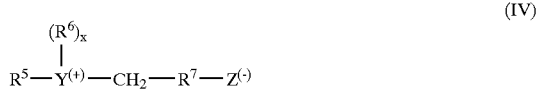 (IV)

wherein $R^5$ denotes a straight-chain or branched alkyl, alkenyl or hydroxyalkyl group with 8 to 18 carbon atoms and from 0 to about 10 ethylene oxide units and from 0 to about 1 glycerol unit, Y denotes an N-, P- or S-containing group, $R^6$ denotes an alkyl or monohydroxyalkyl group with 1 to 3 carbon atoms, x equals 1 when Y is a sulfur atom and x equals 2 when Y is a nitrogen atom or a phosphorus atom, $R^7$ denotes an alkylene or hydroxyalkylene group with 1 to 4 carbon atoms and $Z^{(-)}$ denotes a carboxylate, sulfate, phosphonate or phosphate group.

Other amphoteric surfactants such as the betaines are also suitable for the hair-treatment preparations of the invention. Examples of betaines include $C_8$–$C_{18}$-alkylbetaines, such as cocodimethylcarboxymethylbetaine, lauryldimethylcarboxymethylbetaine, lauryldimethyl-alpha-carboxyethylbetaine, cetyldimethylcarboxymethylbetaine, oleyldimethyl-gamma-carboxypropylbetaine and lauryl-2-bis(2-hydroxypropyl) -alpha-carboxyethylbetaines, $C_8$–$C_{18}$-sulfobetaines, such as cocodimethylsulfopropylbetaine, stearyldimethylsulfopropylbetaine, lauryldimethylsulfoethylbetaine, lauryl-bis(2-hydroxyethyl) sulfopropylbetaine, the carboxyl derivatives of imidazole, the $C_8$–$C_{18}$-alkyldimethylammonium acetates, the $C_8$–$C_{18}$-alkyldimethylcarbonylmethylammonium salts, the $C_8$–$C_{18}$ fatty acid alkylamidobstaines, for example, coco fatty acid amidopropylbetaine, sold, for example in the form of a 30% aqueous solution, by Goldschmidt AG under the tradename Tego® Betaine L7, and the N-coco fatty acid amidoethyl-N-[2-(carboxymethoxy)ethyl]glycerol (CTFA[1] name: cocoamphocarboxyglycinate), sold, for example in the form of a 50% aqueous solution, by Miranol Chemical Co. under the tradename Miranol® C2M.

The suitable cationic polymers are preferably hair-strengthening or hair-conditioning polymers. Suitable polymers of component (C) preferably contain quaternary amino groups. The cationic polymers can be homopolymers or copolymers, with the quaternary nitrogen contained either in the polymer chain or preferably as a substituent in one or more monomers. The ammonium groups-containing monomers can be copolymerized with non-cationic monomers. Suitable cationic monomers are unsaturated compounds capable of undergoing free radical-initiated polymerization and bearing at least one cationic group, particularly ammonium-substituted vinyl-monomers, for example trialkylmethacryloxyalkylammonium, trialkylacryloxyalkylammonium, dialkyldiallylammonium and quaternary vinylarnmonium monomers with cyclic, cationic nitrogen-containing groups, such as pyridinium, imidazolium or quaternary pyrrolidones, for example alkylvinylimidazolium, alkylvinylpyridinium or alkylvinylpyrrolidone salts. The alkyl groups of these monomers are preferably lower alkyl groups such as, for example, $C_1$–$C_7$-alkyl groups and preferably $C_1$–$C_3$-alkyl groups.

The ammonium group-containing monomers can be copolymerized with non-cationic monomers. Suitable comonomers are, for example, acrylamide, methacrylamide, alkylacrylamide, dialkylacrylamide, alkyl methacrylamide and dialkyl methacrylamide, alkyl acrylate, alkyl methacrylate, vinylcaprolactone, vinylcaprolactam, vinylpyrrolidone, vinyl esters, for example vinyl acetate, vinyl alcohol, propylene glycol or ethylene glycol, the alkyl groups of these monomers preferably being $C_1$–$C_7$-alkyl groups and particularly $C_1$–$C_3$-alkyl groups.

Suitable polymers with quaternary amino groups are, for example, the polymers described in the CTFA Cosmetic Ingredient Dictionary under the name polyquaternium, such as methylvinylimidazolium chloride/vinylpyrrolidone copolymer (polyquaternium 16), or (quaternized vinylpyrrolidone/dimethylaminoethyl methacrylate copolymer (polyquaternium 11).

A suitable cationic polymer that can be contained in the composition of the invention is, for example, vinylpyrrolidone/dimethylaminoethyl methacrylate methosulfate copolymer, sold by Gaf Co., USA, under the tradenames Gafquat 755 N and Gafquat® 734, of which Gafquat® 734 is particularly preferred. Other cationic polymers are, for example, the copolymer of polyvinylpyrrolidone and imidazolimine methochloride, sold by BASF, Germany, under the tradename LUVIQUAT® HM 550, the terpolymer of dimethyldiallylammonium chloride, sodium acrylate and acrylamide, sold by Calgon, USA, under the tradename Merquat® Plus 3300, the terpolymer of vinylpyrrolidone, dimethylaminoethyl methacrylate and vinylcaprolactam sold by ISP, USA, under the tradename Gaffix® VC 713, and the vinylpyrrolidone/methacrylamidopropyltrimethylammonium chloride copolymer sold by Gaf under the tradename Gafquat® HS 100.

Suitable cationic polymers derived from natural polymers are the catlonic derivatives of polysaccharides, for example the cationic derivatives of cellulose, starch or guar. Also suitable are chitosan and chitosan derivatives. The cationic polysaccharides have general formula (V)

 (V)

wherein
G denotes an anhydroglucose radical, for example starch anhydroglucose or cellulose anhydroglucose, B denotes a divalent linking group, for example alkylene, oxyalkylene, polyoxyalkylene or hydroxyalkylene, $R_a$, $R_b$ and $R_c$ independently of each other denote alkyl, aryl, alkaryl, arylakyl, alkoxyalkyl or alkoxyaryl, each with up to 18 carbon atoms, the total number of carbon atoms in $R^a$, $R^b$ and $R^c$ preferably being at the most 20;
$X^{(+)}$ denotes a common counterion with the same meaning as in formula (I) and preferably chloride. A cationic cellulose is sold by Amerchol under the name Polymer JR and has the INCI name polyquaternium 10. Another catinric cellulose has the INCI name polyquaternium 24 and is sold by Amerchol under the tradename Polymer LM-200. A suitable cationic guar derivative is sold under the tradename Jaguar® R and has the INCI name guar hydroxypropyltrimonium chloride.

Particularly preferred cationic substances are chitosan, chitosan salts and chitosan derivatives. The chitosans used according to the invention are completely or partially deacetylated chitins. Chitosan is preferably prepared from the chitin contained in crustacean shell wastes, an inexpensive and natural starting material available in large quantities. The molecular weight of chitosan is distributed over a wide range, for example from 20,000 to about 5 million g/mol. Suitable is, for example, a low-molecular-weight chitosan with a molecular weight of 30,000 to 70,000 g/mol. Preferably, however, the molecular weight is higher than 100,000 g/mol and particularly between 200,000 and 700,000 g/mol. The degree of deacetylation is preferably 10 to 99% and particularly 60 to 99%.

A suitable chitosan is, for example, the one sold by Kyowa Oil & Fat, Japan, under the tradename Flonac®. It has a molecular weight of 300,000 to 700,000 g/mol and is 70 to 80% deacetylated. A preferred chitosan salt is chitosoniumpyrrolidonecarboxylate sold, for example, by Amerchol, USA, under the name Kytamer PC. The chitosan contained therein has a molecular weight of about 200,000 to 300,000 g/mol and is 70 to 85% deacetylated. Suitable chitosan derivatives are the quaternized, alkylated or hydroxyalkylated derivatives, for example hydroxyethylchitosan or hydroxybutylchitosan.

The chitosans and chitosan derivatives are preferably in neutralized or partly neutralized form. The degree of neutralization of chitosan or of the chitosan derivative is preferably at least 50% and particularly between 70 and 100%, based on the number of free basic groups. Suitable as neutralization agents are. In principle, all cosmetically tolerated inorganic or organic acids. for example formic, tartaric, malic, lactic, citric, pyrrolidonecarboxylic and hydrochloric acid etc, among which pyrrolidonecarboxylic acid is particularly preferred.

Other suitable cationic hair-care compounds are the cationically modified protein derivatives or cationically modified protein hydrolyzates known, for example, under the INCI names lauryldimonium hydroxypropyl hydrolyzed wheat protein, lauryldimonium hydroxypropyl hydrolyzed casein, lauryldimonium hydroxypropyl hydrolyzed collagen, lauryldimonium hydroxypropyl hydrolyzed keratin, lauryldimonium hydroxypropyl hydrolyzed silk, lauryldimonium hydroxypropyl hydrolyzed soy protein or hydroxypropyltrimonium hydrolyzed wheat, hydroxypropyltrimonium hydrolyzed casein, hydroxypropyltrimonium trimonium hydrolyzed collagen, hydroxypropyltrimonium hydrolyzed keratin, hydroxypropyltrimonium hydrolyzed rice bran protein, hydroxypropyltrimonium hydrolyzed silk, hydroxypropyltrimonium hydrolyzed soy protein and hydroxypropyltrimonium hydrolyzed vegetable protein.

Suitable cationically derivatized protein hydrolyzates are mixtures of substances obtained, for example, by reaction of alkaline, acid or enzymatically hydrolyzed proteins and glycidyltrialkylammonium salts or 3-halo-2-hydroxypropyltrialkylammonium salts. Proteins of vegetable as well as animal origin can be used as starting materials for the protein hydrolyzates. Common starting materials are, for example, keratin, collagen, elastin, soy protein, rice protein, milk protein, wheat protein, silk protein or almond protein. Hydrolysis produces mixtures of substances with a molecular weight ranging from about 100 to about 50,000. The average molecular weights are usually in the range from about 500 to about 1000. Advantageously, the cationically derivatized protein hydrolyzates contain one or two long $C_8$–$C_{22}$-alkyl chains and correspondingly two or one short $C_1$–$C_4$-alkyl chain. Compounds containing one long alkyl chain are preferred.

The hydrophilic group of the hair-care silicone compounds (D) used according to the invention are preferably selected from among hydroxyl groups, primary, secondary or tertiary amino groups, quaternary ammonium groups, alkylene oxide groups, betaine groups or thiosulfate groups.

Suitable and particularly preferred are cationic silicone compounds. These compounds are substituted with cationic or cationizable groups. Suitable cationic silicone compounds have at least one amino group or at least one ammonium group. Suitable silicone polymers with amino groups are known under the INCI name of amodimethicones. These are polydimethylsiloxanes with aminoalkyl groups. The aminoalkyl groups can be lateral or terminal. Suitable aminosilicones are those of general formula (VI)

$$R^8R^9R^{10}Si\text{—}(OSiR^{11}R^{12})x\text{—}(OSiR^{13}Q)y\text{—}OSiR^{14}R^{15}R^{16} \quad (VI)$$

wherein
- $R^8$, $R^9$, $R^{14}$ and $R^{16}$ independently of each other are equal or different and denote $C_1$–$C_{10}$-alkyl, phenyl, hydroxyl, hydrogen, $C_1$–$C_{10}$-alkoxy or acetoxy, preferably $C_1$–$C_4$-alkyl, and particularly methyl, $R^{10}$ and $R^{16}$ independently of each other are equal or different and denote —$(CH_2)_a$—$NH_2$ where a equals 1 to 6, $C_1$–$C_{10}$-alkyl, phenyl, hydroxyl, hydrogen, $C_1$–$C_{10}$-alkoxy or acetoxy, preferably $C_1$–$C_4$-alkyl and particularly methyl;
- $R^{11}$, $R^{12}$ and $R_{13}$ independently of each other are equal or different and denote hydrogen, a $C_1$–$C_{20}$ hydrocarbon possibly containing O atoms and N atoms, preferably $C_1$–$C_{10}$-alkyl or phenyl, more preferably $C_1$–$C_4$-alkyl and particularly methyl;
- O denotes —A—$NR^{17}R^{18}$ or A—$N^+R^{17}R^{18}R^{19}$, wherein A denotes a divalent $C_1$–$C_{20}$-alkylene linking group possibly containing O atoms or N atoms or OH groups, and $R^{17}$, $R^{18}$ and $R^{19}$ independently of each other are equal or different and denote hydrogen, $C_1$–$C_{22}$ hydrocarbon, preferably $C_1$–$C_4$-alkyl or phenyl. Preferred radicals for O are —$(CH_2)_3$—$NH_2$, —$(CH_2)_3$$NHCH_2CH_2NH_2$, —$(CH_2)_3OCH_2CHOHCH_2NH_2$, —$(CH_2)_3N(CH_2CH_2OH)_2$, —$(CH_2)_3NH_3^+$ and —$(CH_2)_3OCH_2CHOHCH_2N^+(CH_3)_2R^{20}$, wherein $R^{20}$ denotes a $C_1$–$C_{22}$ alkyl group possibly also containing OH groups; x denotes a numeral between 1 and 10,000 and preferably between 1 and 1000, and y denotes a numeral between 1 and 500 and preferably between 1 and 50.

The molecular weight of the aminosilicones is preferably between 500 and 100,000. The amine content (meq/g) is preferably in the range from 0.05 to 2.3 and particularly from 0.1 to 0.5.

Suitable silicone polymers with two terminal quaternary ammonium groups are known under the INCI name quaternium 80. These are dimethylsiloxanes with two terminal aminoalkyl groups. Suitable quaternary aminosilicones are those of general formula (VII)

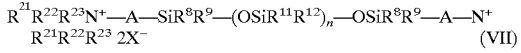

$$R^{21}R^{22}R^{23}N^+\text{—}A\text{—}SiR^8R^9\text{—}(OSiR^{11}R^{12})_n\text{—}OSiR^8R^9\text{—}A\text{—}N^+ \\ R^{21}R^{22}R^{23} \; 2X^- \quad (VII)$$

A has the same meaning as in formula (VI) hereinabove and is preferably —$(CH_2)_3OCH_2CHOHCH_2N^+(CH_3)_2R^{20}$, wherein $R^{20}$ denotes a $C_1$–$C_{22}$-alkyl radical possibly also containing OH groups,
- $R^8$, $R^9$, $R^{11}$ and $R^{12}$ have the same meaning as in formula (VI) hereinabove and preferably denote methyl;
- $R^{21}$, $R^{22}$ and $R^{23}$ independently of each other denote $C_1$–$C_{22}$-alkyl radicals possibly also containing hydroxyl groups, with preferably at least one of the radicals having at least 10 carbon atoms and the other radicals having from 1 to 4 carbon atoms;

n is a numeral from 0 to 200 and preferably from 10 to 100. Such diquaternary polydimethylsiloxanes are sold by Goldschmidt, Germany, under the tradenames Abil® Quat 3270, 3272 and 3274.

Suitable silicones with alkylene oxide groups are polydimethylsiluxanes with polyoxyalkylated substituents, particularly silicones modified with polypropylene oxide, polyethylene oxide or a mixture thereof. The alkylene oxide groups can be lateral or terminal, and the compounds can be polydimethylsiloxane/polyalkylene oxide block copolymers. The siloxanes modified with alkylene oxides are also referred to as dimethylsiloxane-glycol copolymers or dimethicone copolyols. Suitable silicones with hydroxyl groups are the dimethiconols. These are polydimethylsiloxanes with hydroxyl end groups. Suitable silicones with thiosulfate groups are known under the INCI name dimethicone/sodium PG propyidimethicone thiosulfate copolymer.

The composition of the invention is preferably prepared in an aqueous or aqueous alcoholic medium and is characterized particularly by clarity and transparency, For this reason, the composition is advantageously placed into visually attractive packaging made of transparent or translucent print-resistant material. Suitable packaging materials are, in particular, glas and transparent or translucent plastics such as, for example, polyethylene terephthalate. The composition can contain as the alcohol, in particular, a lower alcohol with 1 to 4 carbon atoms usually employed for cosmetic purposes, for example ethanol and isopropanol. The water content is preferably from 40 to 95 wt.% and particularly from 60 to 90 wt. %. The alcohol content is preferably from 1 to 30 wt.% and particularly from 5 to 20 wt. %. Other, particularly preferred water-soluble solvents or moisturizers are the polyhydric alcohols, particularly those with 2 to 4 carbon atoms, for example glycerol, ethylene glycol or propylene glycol, in an amount from 0.1 to 10 wt. % and preferably from 0.5 to 5 wt. %. Purely aqueous formulations are particularly preferred.

In a preferred embodiment, the composition of the invention also contains at least one nonionic surfactant. Suitable nonionic surfactants are, for example, the nonionic emulsifiers listed in the "International Cosmetic Ingredient Dictionary and Handbook", 7th edition, volume 2, in the section on "Surfactants-Emulsifying Agents". Suitable nonionic surfactants are preferably those selected from among the ethoxylated fatty acids with 10 to 26 carbon atoms, ethoxylated monohydric or polyhydric alcohols with 1 to 6 carbon atoms, ethoxylated fatty alcohols with 10 to 26 carbon atoms, ethoxylated hydrogenated or non-hydrogenated castor oil, alkyl polyglucosides, glyceride alkoxylates, fatty acid glyceride polyalkylene glycol ethers or fatty acid partial glyceride polyalkylene glycol ethers, each with less than 30 alkylene glycol units, for example polyethylene glycol-(7)-glyceryl cocoate, polyglycolamides, fatty acid sugar esters, ethoxylated fatty acid sugar esters and partial glycerides. The degree of ethoxylation of the ethoxylated surfactants is usually from 1 to 400, preferably from 2 to 200 and particularly from 3 to 25.

In a preferred embodiment, the composition of the invention contains only water-soluble surfactants and emulsifiers, i.e., surfactants which at a 1 wt. % water content are clear and soluble at 20° C.

Preferred nonionic surfactants are, in particular, fatty alcohol ethoxylates. Suitable area, for example, alcohols with 10 to 18, and preferably 10 to 16 carbon atoms, and a degree of ethoxylation of, preferably, 2 to 200 and particularly 3 to 25. The additional nonionic surfactants are preferably used in an amount from 0.01 to 5 wt. %.

In another preferred embodiment, the composition of the invention contains at least one film-forming, hair-strengthening synthetic or natural polymer. This additional polymer can be nonionic, anionic or amphoteric and is preferably used in an amount from 0.5 to 10 wt. %. By film-forming, hair-strengthening polymers are meant polymers which when used in a 0.1 to 5% aqueous, alcoholic or aqueous-alcoholic solution are capable of depositing a polymer film on the hair thus strengthening the hair.

Moreover, the composition of the invention can additionally contain additive ingredients commonly used in hair-treatment compositions, for example non-strengthening nonionic polymers, non-strengthening anionic polymers and non-strenghtening natural polymers or a combination thereof, preferably in an amount from 0.01 to 10 wt. %; perfume oils, preferably in an amount from 0.01 to 5 wt. %; wetting agents or emulsifiers from the classes of anionic, cationic, amphoteric or nonionic surface-active substances, preferably in an amount from 0.01 to 10 wt. %; moisturizers; preservative: bactericidal and fungicidal materials, for example 2,4,4-trichloro-2-hydroxydiphenyl ether, parabens or methylchloroisothiazolinone, in an amount from 0.01 to 1.0 wt. %; buffering agents, for example sodiumn citrate or sodium phosphate, in an amount from 0.1 to 1.0 wt. %; tinting agents, for example fluorescein sodium salt, in an amount from about 0.1 to 1.0 wt. %; hair-care agents, for example vegetable and herb extracts, protein hydrolyzates, silk hydrolyzates or lanolin derivatives in an amount from 0.1 to 5 wt. %; light-protective agents, antioxidants, free radical scavengers, antidandruff agents, fatty alcohols, luster-imparting agents, vitamins and regreasing agents, in an amount from 0.01 to 10 wt. %.

The composition of the invention can have a pH from 2.0 to 9.5. Particularly preferred are weakly acidic pH values between 4.5 and less than 7, especially 5.5 to 6.5. When the composition of the invention is in the acidic range, it can contain an organic or inorganic acid, for example formic, tartaric, malic, maleic, fumaric, glyoxylic, pyrrolidonecarboxylic, citric, lactic, sulfuric, acetic, hydrochloric or phosphoric acid atc.

To use the composition of the invention, an amount thereof sufficient for the desired conditioning effect is distributed in or on dry hair or, after the hair has been washed, in or on the wet or moist hair. The amount to be used depends on the hair fullness and typically is between 1 and 25 g. In the preferred use as a rinse product, the hair is rinsed after a sufficient exposure time of, for example, 1 to 15 minutes. It is then optionally combed, or styled into a hair-do and then dried. In the use as a leave-in product, the hair is not rinsed after the application of the composition.

The following examples will explain the object of the invention in greater detail.

EXAMPLE 1

Clear Hair Treatment for Damaged Hair

| | |
|---|---|
| 3.0 g | of Arquad ® 12–25 (25%, lauryltrimonium chloride) |
| 2.0 | of Abil ® 9950 (30%, dimethicone propyl PG betaines) |
| 1.1 g | of Pure Thix ® HH (polyether 1) |
| 0.5 g | of Brij ® 30 (laureth 4) |
| to 100 g | water |

Containers are filled with the composition containing 8 wt. % of dimethyl ether, based on the total composition.

EXAMPLE 2

Clear Hair Rinse for Permanently Waved Hair

| | | |
|---|---|---|
| 0.1 g | of Arquad ® 12–50 (50%, lauryltrimonium chloride) | |
| 0.6 g | of Tegobetaine ® (30% in water, cocamidopropyl betaine) | |
| 0.8 g | of Abil ® Quat 3272 (50% in propylene glycol, quaternium 80, diquaternary silicone) | |
| 0.8 g | of Pure Thix ® L (PEG 180/octoxynol 40/TMMG copolymer) | |
| 0.2 g | of glyoxylic acid (1% solution) | |
| to 100 g | water | |

Containers are filled with the composition containing 2 wt. % of propane/butane, based on the total composition, and 6 wt. % of dimethyl ether, based on the total composition.

EXAMPLE 3

Clear Leave-in Treatment

| | |
|---|---|
| 1.0 g | of tallow trimonium chloride |
| 2.0 g | of Abil ® S 201 (30% in isopropanol/water, dimethicone/sodium PG propyldimethicone thiosulfate copolymer) |
| 1.1 g | of Pure Thix ® M (PEG 180/laureth 50/TMMG copolymer) |
| 3.0 g | of Luviquat ® FC 905 (40% in water, polyquaternium 16) |
| to 100 g | water |

Containers are filled with the composition containing 5 wt. % of dimethyl ether, based on the total composition.

EXAMPLE 4

Clear Hair Treatment for Disentangling Hair

| | |
|---|---|
| 2.5 g | of Arquad ® 12–50 (50%, lauryltrimonium chloride) |
| 1.8 g | of Abil ® Quat 3270 (50% in propylene glycol, quaternium 80, diquaternary silicone) |
| 1.3 g | of Pure Thix ® HH (polyether 1) |
| 0.3 g | of Brij ® (laureth 4) |
| 0.2 g | of citric acid (1% solution) |
| to 100 g | water |

Containers are filled with the composition containing 10 wt. % of dimethyl ether, based on the total composition.

EXAMPLE 5

Clear Hair Rinse—Unusually Mild

| | |
|---|---|
| 0.8 g | of Arquad ® 12–25 (25%, lauryltrimonium chloride) |
| 1.0 g | of Dow Corning ® 193 (dimethicone copolyol) |
| 1.0 g | of Pure Thix ® M (PEG 180/laureth 50/TMMG copolymer) |
| 0.5 g | of Rewoteric ® AM CAS (50% in water, cocoamidopropylhydroxysultains) |
| to 100 g | water |

Containers are filled with the composition containing 6 wt. % of dimethyl ether, based on the total composition, and 3 wt. % of F 152a, based on the total composition.

EXAMPLE 6

Clear Leave-in Treatment

| | |
|---|---|
| 1.0 g | of Arquad ® 12–50 (50%, lauryltrimonium chloride) |
| 2.0 g | of Abil ® 8863 (dimethicone copolyol) |
| 0.9 g | of Pure Thix ® HH (polyether 1) |
| 0.5 g | of Luviskol ® K30 (polyvinylpyrrolidone) |
| to 100 g | water |

Containers are filled with the composition containing 5 wt. % of dimethyl ether, based on the total composition.

What is claimed is:

1. A composition for a hair treatment preparation, wherein said composition comprises at least one nonionic, amphiphilic associative thickener in a cosmetic carrier, at least one propellant; and at least one hair care agent, said at least one hair care agent consisting of at least one cationic surfactant and/or at least one silicone compound with at least one hydrophilic group;

wherein said at least one nonionic, amphiphilic associative thickener is at least one reaction product of acid-catalyzed polycondensation of an at least difunctional aminoplast monomer, an at least difunctional alkylene polyether and a monofunctional compound with at least one hydrophobic group.

2. The composition as defined in claim 1, wherein said at least one nonionic, amphiphilic associative thickener is at least one reaction product of acid catalyzed reaction of a glycoluril derivative, a polyalkylene glycol and an alkoxylated hydrocarbon.

3. The composition as defined in claim 1, wherein said at least one nonionic, amphiphilic associative thickener is selected from the group consisting of polyether 1, PEG 180/octoxynol 40/TMMG copolymer and PEG 180/laureth 50/TMMG copolymer.

4. The composition as defined in claim 1, wherein said at least one propellant is selected from the group consisting of n-butane, isobutene, propane, dimethyl ether and fluorohydrocarbons.

5. The composition as defined in claim 1, wherein said at least one cationic surfactant is at least one cationic surface-active compound of formula (III)

$$N^{(+)}R^1R^2R^3R^4X^{(-)} \qquad \text{(III)}$$

wherein each of said $R^1$, $R^2$, $R^3$ and $R^4$ represent, independently of each other, an aliphatic group, an aromatic group, an alkoxy group, a polyalkylene group, an alkylamido group, a hydroxyalkyl group, an aryl group or an alkyaryl group, each of said group having from 1 to 22 carbon atoms, and $X^{(-)}$ denotes an anion.

6. The composition as defined in claim 1, further comprising at least one cationic polymer selected from the group consisting of methylvinylimidazolium chloride/vinylpyrrolidone copolymers, quaternized vinylpyrrolidone/dimethyl-aminoethyl methacrylate copolymers, cationically derivatized polysaccharides, chitosan, chitosan salts and chitosan derivatives.

7. The composition as defined in claim 1, wherein said at least one silicone compound is selected from the group consisting of silicone compounds with at least one hydroxy group, silicone compounds with at least one primary amine group, silicone compounds with at least one secondary amine group, silicone compounds with at least one tertiary amine group, silicone compounds with at least one quaternary ammonium group, silicone compounds with at least one alkylene oxide group, silicone compounds with at least one betaine group and silicone compounds with at least one thiosulfate group.

8. The composition as defined in claim 1, wherein said at least one silicone compound with said at least one hydrophilic group is a silicone compound with a cationic group, a silicone compound with a hydroxy group, a siloxane/polyoxyalkylene copolymer or an amino-substituted siloxane.

9. A hair treatment preparation containing a composition, said composition being in an optically clear form;
   wherein said composition comprises at least one nonionic, amphiphilic associative thickener in a cosmetic carrier; at least one propellant, at least one cationic surfactant and at least one silicone compound with at least one hydrophilic group; and
   wherein said at least one nonionic, amphiphilic associative thickener is at least one reaction product of acid-catalyzed polycondensation of an at least difunctional aminoplast monomer, an at least difunctional alkylene polyether and a monofunctional compound with at least one hydrophobic group.

10. A hair treatment product consisting of a transparent or translucent package and a composition in an optically clear form, said composition being contained in said transparent or translucent package;
    wherein said composition comprises at least one nonionic, amphiphilic associative thickener in a cosmetic carrier; at least one propellant, at least one cationic surfactant and at least one silicone compound with at least one hydrophilic group; and
    wherein said at least one nonionic, amphiphilic associative thickener is at least one reaction product of acid-catalyzed polycondensation of an at least difunctional aminoplast monomer, an at least difunctional alkylene polyether and a monofunctional compound with at least one hydrophobic group.

11. A composition for a hair treatment preparation, said composition comprising
    at least one nonionic, amphiphilic associative thickener in a cosmetic carrier;
    at least one propellant;
    at least one cationic surfactant; and
    at least one silicone compound with at least one hydrophilic group;
    wherein said at least one nonionic, amphiphilic associative thickener is at least one reaction product of acid-catalyzed polycondensation of an at least difunctional aminoplast monomer, an at least difunctional alkylene polyether and a monofunctional compound with at least one hydrophobic group.

12. A composition for a hair treatment preparation, said composition consisting essentially of
    at least one nonionic, amphiphilic associative thickener in a cosmetic carrier;
    at least one propellant; and
    at least one additive ingredient selected from the group consisting of cationic hair care substances, silicone compounds with at least one hydrophilic group, nonionic surfactants, film-forming hair-fixing polymers, non-fixing nonionic polymers, non-fixing anionic polymers, non-fixing natural polymers, perfume oils, wetting agents, emulsifiers, moisturizers, preservatives, bactericidal materials, fungicidal materials, buffering agents, vegetable extracts, herb extracts, protein hydrolyzates, silk hydrolyzates, lanolin derivatives, light-protective agents, antioxidants, free radical scavengers, antidandruff agents, fatty alcohols, luster-imparting agents and vitamins;
    wherein said at least one nonionic, amphiphilic associative thickener is at least one reaction product of acid-catalyzed polycondensation at an at least difunctional aminoplast monomer, an at least difunctional alkylene polyether and a monofunctional compound with at least one hydrophobic group.

* * * * *